United States Patent [19]
Atwood et al.

[11] Patent Number: 5,711,927
[45] Date of Patent: Jan. 27, 1998

[54] METHOD FOR THE PURIFICATION AND SEPARATION OF FULLERENES

[76] Inventors: Jerry L. Atwood, 1204 Indian Hills, Tuscaloosa, Ala. 35406; Colin L. Raston, 42 Lancelot St., Tennyson, Qld, 4105, Australia

[21] Appl. No.: 411,073

[22] Filed: Mar. 27, 1995

Related U.S. Application Data

[63] Continuation of Ser. No. 213,696, Mar. 16, 1994, abandoned.

[51] Int. Cl.$^6$ ............................................. C01B 31/02
[52] U.S. Cl. ............................ 423/445 B; 423/DIG. 39; 423/DIG. 40
[58] Field of Search .................. 423/445 B, DIG. 39, 423/DIG. 40

[56] References Cited

U.S. PATENT DOCUMENTS 5,338,529  8/1994  Pirkle et al. ........................ 423/445 B

OTHER PUBLICATIONS

Bauer, L.J., et al. "Calixarenes ...", J. Am. Chem. Soc., 1985, vol. 107, 6063–6069.

Ermer, O. "3:1 Molecular Complex of Hydroquinone and $C_{60}$", Helvetica Chimica Acta, vol. 74, 1991, pp. 1339–1351.

Shriner, et al. "Systematic Identification of Organic Compounds", 6th ed. Wiley:New York (1980), pp. 371–374.

Cabrera, et al. "High Performance LC Separation of Fullerenes Using ... Gamma Cyclodextrin", J. Chromatography, vol. 644 (1993) pp. 396–399.

Diederich, F., et al. "$C_{60}$ and $C_{70}$ in a Basket? ..." Angew. Chem. Int. Ed. Eng., vol. 31, #12 (1992), pp. 1599–1602.

Verhoeven, J.W., et al. "Supramolecular Encapsulation of $C_{60}$ in a Water Soluble Calixarene ...". Recueil desTravaux Chimiques,des Pays–Bas, vol. III, pp. 531–532 (1992).

Welch, C.J., et al. "Progress in the Design of Selectors ..." J. Chromatography vol. 609 (1992), pp. 89–101.

*Primary Examiner*—Steven Bos
*Assistant Examiner*—Peter T. DiMauro
*Attorney, Agent, or Firm*—William D. Jackson; Locke Purnell Rain Harrell

[57] ABSTRACT

This invention relates to a method of purifying afullerenes by recrystallization of a fullerene-complexing agent complex and to a fullerene-complexing agent complex.

33 Claims, 3 Drawing Sheets

METHOD FOR THE PURIFICATION AND SEPARATION OF FULLERENES

This application is a Continuation of application Ser. No. 081213,696, filed on Mar. 16, 1994, now abandoned.

BACKGROUND OF THE INVENTION

1. Field of the Invention

This invention relates to a method of purifying fullerenes by recrystallization of a fullerene-complexing agent complex and to a fullerene-complexing agent complex.

2. Discussion of the Background

Since their discovery by R. E. Smalley (in *Physical and Theoretical Chemistry*, Vol. 68. Elsevier Science: New York, 1990 pp. 1–68), molecular fullerenes have received considerable interest with anticipated applications in such varied fields such as polymers, batteries, high-temperature superconductors, catalysts, drug delivery systems and pharmaceuticals. Other applications include optical devices based on fullerene photoconductivity or photovoltaic properties, carbides, chemical sensors, gas separation devices, thermal insulation, diamonds, diamond thin films and hydrogen storage. In fact, fullerenes are even reported to be useful as a pigment for toner compositions (U.S. Pat. No. 5,188,918). In particular $C_{60}$, also referred to as buckminsterfullerene, which has the molecular geometry of a truncated icosahedron, and thus resembles a molecular sized soccer ball, has received tremendous inquiry throughout the scientific community and the population at large.

However, the difficulties in the preparation, isolation and purification of fullerene materials has greatly hindered their commercial exploitation. Presently, fullerenes are sold commercially from Texas Fullerenes Corporation, 2415 Shakespeare Suite 5, Houston, Tex. 77030–1034, Materials and Electrochemical Research (MER) Corporation, 7960 South Kolb Road, Tucson, Ariz. 85706, and Research Materials, Inc., 1667 Coal Boulevard, Golden, Colo. 80401. A mixture of $C_{60}/C_{70}$ (i.e., fullerite) is availible from the Aldrich Chemical Company for a price of $900 per gram.

The high cost of these materials is reflective of the difficulties in preparing, isolating and purifying these materials. It is presently not possible to efficiently purify fullerenes, on a large scale, in part due to inherent losses attributable to chromatographic techniques, arising from irreversible absorption of the fullerene material onto the stationary phase.

Ajie et al (*J.Phys Chem* (1990) 94, 8630–8633) report the separation of $C_{60}$ and $C_a$ by hexane chromatography on neutral alumina. Purified fractions of 99.85% $C_{60}$ and >99% $C_{70}$ were obtained. The yield of purified material was not reported.

Hawkins et al (*J. Org. Chem.* (1990) 55, 6250–6252) report the separation of $C_{60}$ and $C_{70}$ by preperative HPLC on a Pirkle phenylglycine-based column with hexanes as solvent. Amounts of about 0.5 mg per injection could be purified.

Scrivens et al (*J, Am. Chem. Soc.*, (1992) 114, 7917–7919) report the purification of $C_{60}$ on a column of alkaline decolorizing carbon Norit-A and silica gel. 68% of a possible 75% of $C_{60}$ was obtained.

Khemani et al (*J.Org. Chem.* (1992) 57, 3254–3256) report the isolation of $C_{60}$ and $C_{70}$ by soxhlet chromatography with hexanes.

In addition to the numerous chromatographic procedures reported, simple crystallization procedures have also been reported.

Coustel et al (*J. Chem. Soc Chem. Commun.* 1992, 1402) report that $C_{60}$ crystallizes during toluene soxhlet extraction of fullerenes from soot. About 40 wt % of the fullerenes in the soot could be obtained as mostly $C_{60}$ with trace impurities of $C_{70}$. The trace impurities of $C_{70}$ can be removed by a second recrystallization from a toluene soxhlet. By this method 99.99% pure $C_{60}$ can be obtained. However, while high purity $C_{60}$ could be obtained, the process is very inefficient.

Prakash et al have reported (*Chemical and Engineering News* Sep. 20, 1993, p. 32) that $C_{60}$ can be purified from $C_{70}$ by precipitation of an $AlCl_3$-$C_{60}$ complex, from $CS_2$. $C_{60}$ of greater than 99.9% purity can be obtained by this method. However the use of $CS_2$ is not desirable due to its flammability and toxicity.

Calixarenes are complex compounds containing a metacyclophane framework. Although some applications for some types of calixarenes compounds have been developed, research into calixarene chemistry is still progressing (see for Example Gutsche, *Calixarenes, Royal Soc. Chem.* 1989).

Depending upon the reaction conditions, the condensation of o-dimethoxybenzene with formaldehyde has been shown to yield both a cyclic trimer, cyclotriveratrylene (CTV), and the analogous tetrameric species, cyclotetraveratrylene (CTTV). Apart from the utility of compounds derived from CTV in the synthesis of cryptophanes and other effective small molecule complexing agents, CTV and CTTV also exhibit an extensive host-guest chemistry. These molecules are meant to be typical bowl-, cup-, or cavitand-shaped molecules as hosts.

Within the area of host-guest chemistry, calixarenes have been investigated in terms of their interaction with fullerene compounds (*Williams et al Recueil Des Travaux Chimiques des Pays-bas*, 111 531–532 1992)). This reference reports the selective formation of a complex of $C_{60}$ with a water-soluble calix[8]aryloxy-49, 50, 51, 52, 53, 54, 55, 56-octakis-(propane-3-sulphonate). The calixarene host is functionalized with a 3-propanesulphonate group to provide water-solubility to the calixarene. However, since the material is not soluble in organic solvents, the calixarene is able to selectively extract $C_{60}$, from a toluene mixture of $C_{60}/C_{70}$, into the aqueous phase. The purified $C_{60}$ can be obtained by toluene extraction of the dried aqueous residue. Thus the reference reports a method of purifying $C_{60}$, by solubilization and extraction.

In spite of these limited report, a simple and economical method of purifying fullerenes remains the subject of vigorous research. A simple and economical method of purifying fullerenes by recrystallization would be welcome.

SUMMARY OF THE INVENTION

Accordingly, one object of this invention is to provide a novel method of purifying fullerenes, through the recrystallization of complexes formed with a complexing agent.

Another embodiment of this invention is directed to a method of purifying fullerite through the recrystallization of a complex formed with a complexing agent.

Another embodiment of the invention is directed to a process of separating and purifying $C_{60}$, and higher fullerenes, by recrystallization from a complex formed with a complexing agent.

Another embodiment of the invention is directed to a process of separating and purifying $C_{60}$, and higher fullerenes, by recrystallization from a complex formed with an immobilized complexing agent.

Another embodiment of the present invention is directed to a complex of fullerene and a complexing agent, which is soluble in an organic solvent.

The objects of the present invention are provided for by Applicants' discovery that calixarenes, cycloveratrylenes and other organic complexing agents allow for the selective complexation of fullerenes, which can then be purified by recrystallization from an organic solvent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Throughout the specification, the terms $C_{60}$ and fullerene-60 will be used interchangably. Also the terms $C_{70}$ and fullerene-70 will be used interchangably.

According to the present process a mixture of crude fullerene is contacted with a complexing agent. The nature of the fullerene being purified, will determine which complexing agent should be used.

For example suitable complexing agents are the calixarenes. Suitable calixarenes for practicing the present invention are of the formula I

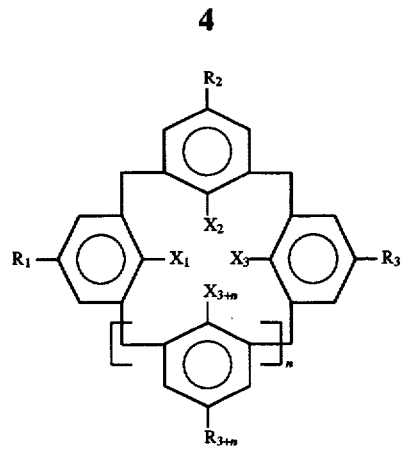

wherein $R_1$-$R_{3+n}$ are each independently H, primary $C_{1-20}$ alkyl, secondary $C_{3-20}$ alkyl, tertiary $C_{4-20}$ alkyl, $C_{1-20}$ alkoxy, $C_{1-20}$ thioalkyl, $C_{6-20}$ aryl, $C_{6-20}$ aryloxy, $C_{6-20}$ aryl, nitro, halogen and $CH_2NR^1_2$ where $R^1$ is a $C_{1-20}$ alkyl;

$X_1$-$X_{3+n}$ are each independently H, OH, SH, $C_{1-20}$ alkoxy, $C_{1-20}$ thioalkyl, $C_{6-20}$ aryloxy, $OC(O)C_{1-20}$ alkyl and $C_{2-20}$ alkenyloxy; and n is an integer of 1 to 11, preferably 1–7, more preferably 1–5.

Preferably $R_1$- $R_{3+n}$ may be hydrogen, methyl, ethyl, propyl, isopropyl, butyl, iso-butyl, sec-butyl, tert-butyl, phenyl, xylyl, phenyoxy, naphthyl, benzyl, fluorine, chlorine, bromine and iodine, methoxy, ethoxy, propoxy butoxy, N,N- dimethyl methyleneamine, N,N-diethyl methyleneamine, N,N- dipropyl methyleneamine, N,N-diphenyl methyleneamine, $C_{6-20}$ aryl, $NO_2$ or $CH_2NR^1_2$ where $R^1$ is a $C_{1-20}$ alkyl.

Preferably $X_1$-$X_{3+n}$ may be H, OH, methoxy, ethoxy and propoxy.

More specifically, suitable calixarenes are calix[4]arene, calix[5]arene, calix[6]arene, calix[7]arene, calix[8]arene, calix[9]arene and calix[10]arene as well as para substituted derivatives thereof.

The specific substituents located at the para position of the aromatic ring will in part influence the selectivity of the specific calixarene to the fullerene. For example, p-Bu$^t$-calix[8]arene selectively binds $C_{60}$, while, p-Bu$^t$-calix[6]arene binds mostly $C_{70}$. Calix[6]arene binds to both $C_{60}$ and $C_{70}$. In addition, p-phenylcalix[4]arene binds $C_{60}$ while p-Bu$^t$-calix[4]arene does not bind to $C_{60}$. Accordingly the size of the para substituent will affect the size of the calixarene cavity and the selectivity of the calixarene for a specific fullerene.

Figure 1:
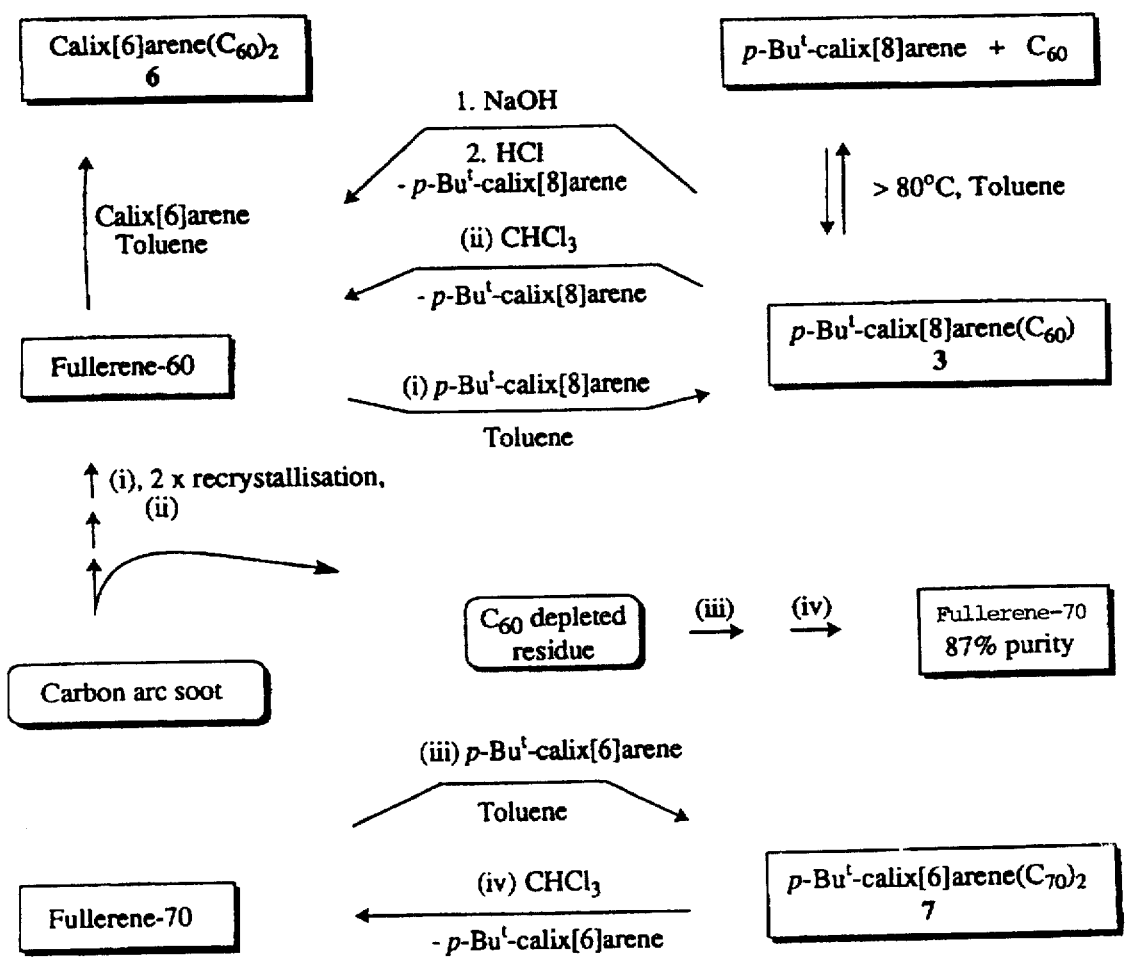
FIG. 1 shows a purification scheme for $C_{60}$ and $C_{70}$ fullerene by complexation with p-Bu$^t$-calix[8]arene, p-Bu$^t$-calix[6]arene and calix[6]arene.
Figure 2:
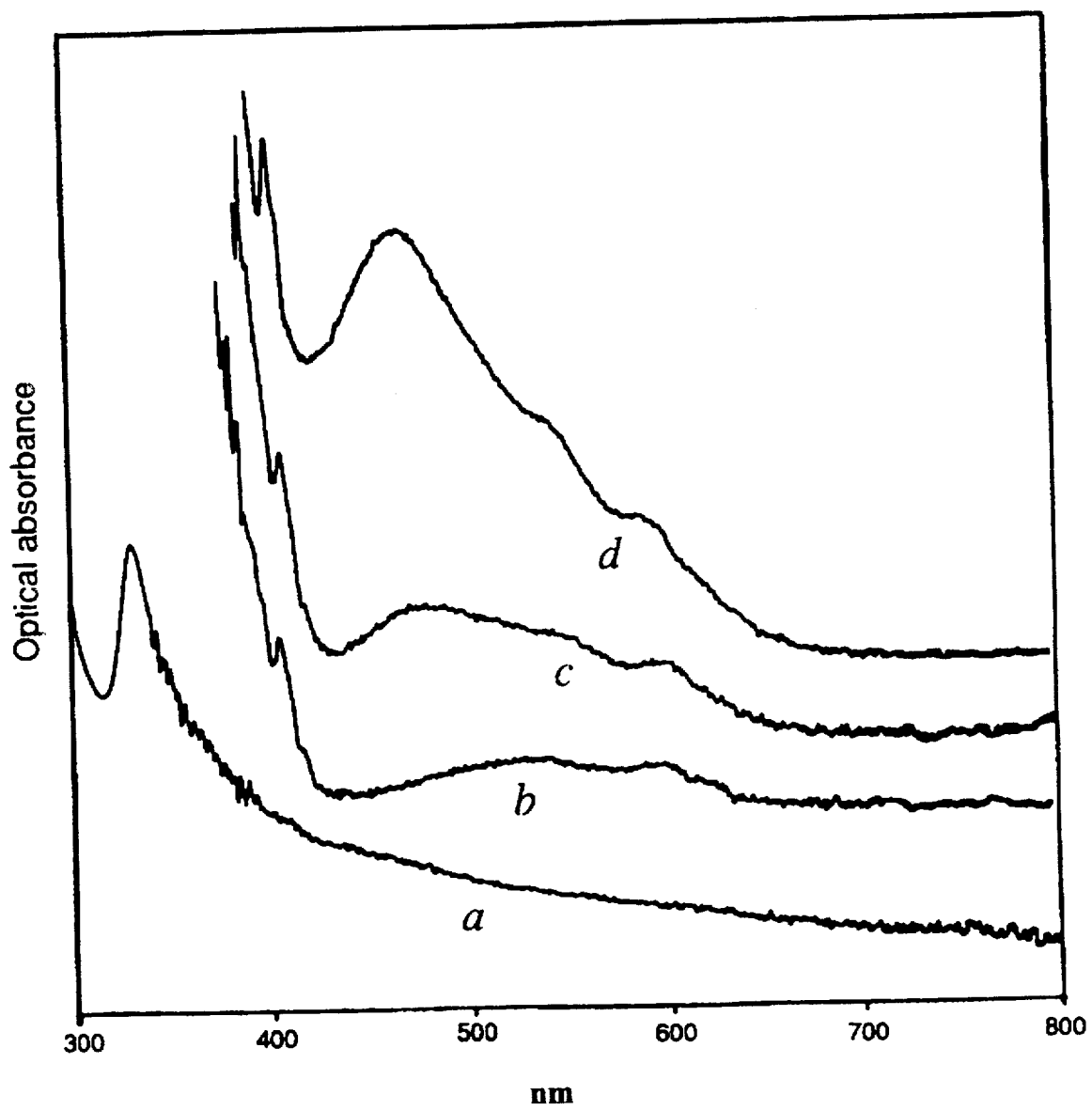
FIG. 2 shows the UV-visible absorption spectrum of (a) a carbon tetrachloride solution of a complex of p-Bu$^t$-calix[8]arene with $C_{60}$ 3, (b) a toluene solution of a complex of p-Bu$^t$-calix[8]arene with $C_{60}$ 3, (c) a toluene solution of the precipitate formed from crude fullerene mixtures and p-Bu$^t$-calix[8]arene, and (d) a dichloromethane solution of fullerenes recovered from the mother liquors from the first recrystallization of the complex in (c).

Toluene solutions of p-Bu$^t$-calix[8]arene form a sparingly soluble brown/yellow precipitate in the presence of a toluene solution of purified fullerene-60, analyzing as the 1:1 complex. In the presence of toluene solutions of crude fullerene mixtures, a similar precipitate results which was shown by UV-visible spectroscopy (see FIG. 2) and FAB mass spectrometry to be the same complex containing some fullerene-70. The fullerene mixture retrieved from this precipitate by addition of chloroform (see FIG. 1) was shown by HPLC to be based exclusively on fullerene-60 and fullerene-70, 89% and 11% respectively, which represents ca 90% of the fullerene-60 content of the soot. One recrystallization of the precipitate, from toluene, enriched the fullerene-60 content to 96% with ca 10% of the fullerenes in the mother liquor as 26% fullerene-60 and 74% fullerene-70. A second recrystallization gave >99.5% purity fullerene-60, again with ca 10% of the fullerenes in the mother liquor, as 72% fullerene-60 and 28% fullerene-70.

The recovery of high purity fullerene-60 is essentially quantitative if the mother liquor solutions are recycled back to the crude fullerene mixture, along with p-Bu$^t$-calix[8]arene recovered from chloroform degradation of the complex. In addition, p-Bu$^t$-calix[8]arene has a higher affinity towards fullerene-60 relative to fullerene-70, noting purified fullerene-70 does not readily form a complex with p-Bu$^t$-calix[8]arene.

Figure 3:
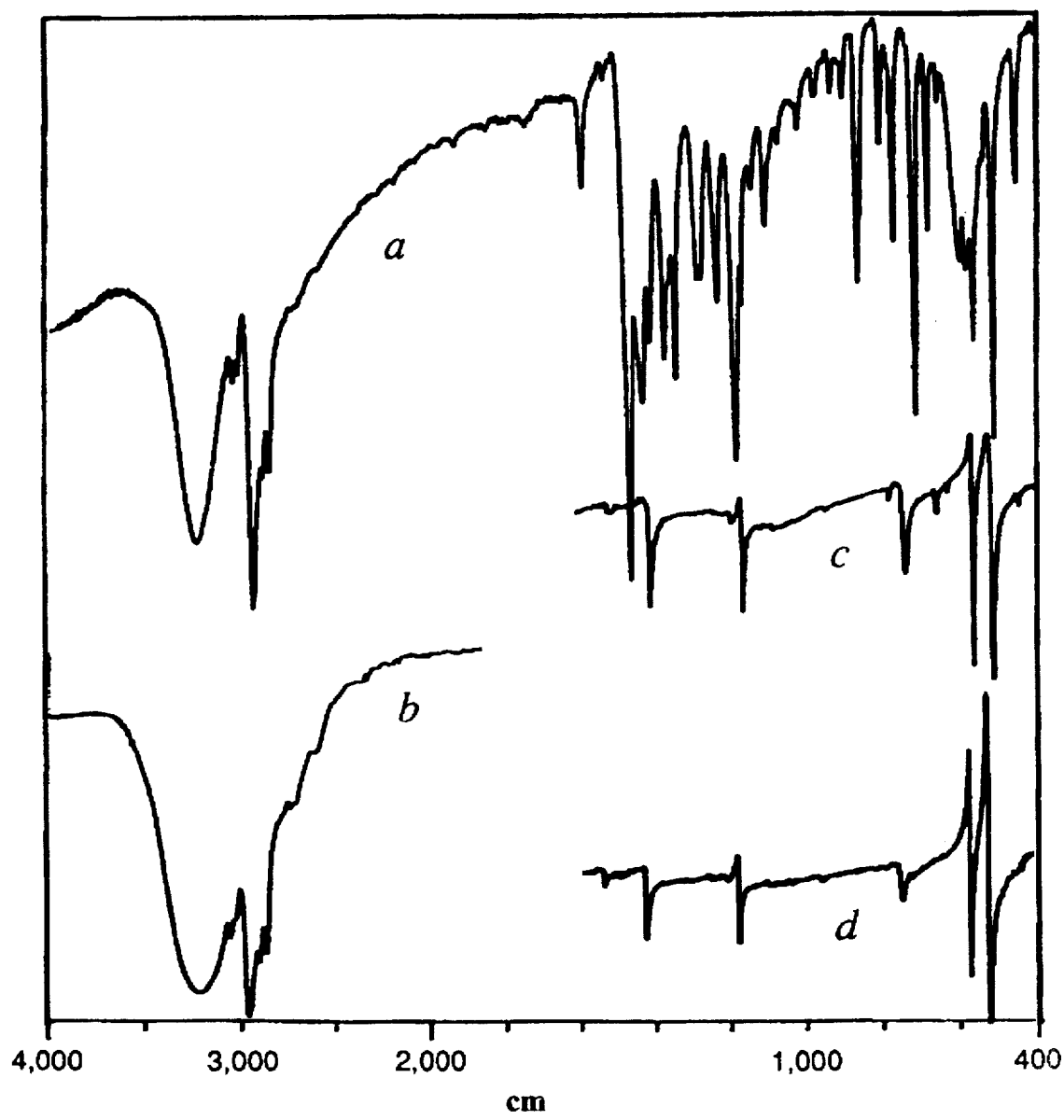
FIG. 3 provides an infrared spectra (KBr disk) of (a) a complex of p-Bu$^t$-calix[8]arene with $C_{60}$ 3, (b) p-Bu$^t$-calix[8]arene, excluding the fingerprint region which matches the spectrum of a complex of p-Bu$^t$-calix[8]arene with $C_{60}$ 3 except for the bands corresponding to fullerene-60, (c) the fullerene mixture derived from decomposition of the precipitate formed between p-Bu$^t$-calix[8]arene and a toluene solution of crude fullerene, and (d) fullerene-60 purified by complexation/recrystallization (the band of 760 cm$^{-1}$ corresponds to chloroform).

The IR spectrum of complex 3 is a superposition of that for the calixarene and fullerene-60, except for the $v_{OH}$ stretching region (see FIG. 3). Nevertheless the H-bonding network is retained and the fullerene most likely resides in the cavity, as a 'ball and socket' nano-structure.

Calix[6]arene forms a sparingly soluble 1:2 complex with fullerene-60 in toluene, complex 6, (see FIG. 1) but not with fullerene-70 in the same solvent under the same conditions. Treatment of a toluene solution of crude fullerenes with the same calixarene yields a highly crystalline material containing both fullerene-60 and fullerene-70, 67% and 33% respectively (HPLC analysis of NaOH treated toluene solutions of the complex). Thus there is no discrimination between the two fullerenes. It has also been found that p-Bu$^t$-calix[6]arene, forms a 1:2 complex with fullerene-70, complex 7 (see FIG. 1). Treatment of the fullerene residue, depleted of most of the fullerene-60 as complex 3, with p-Bu$^t$-calix[8]arene yields a precipitate which on treatment with chloroform affords a material rich in fullerene-70 (87% along with 13% fullerene-60).

The synthesis of calixarenes and substituted calixarenes is well known to those of ordinary skill in the art and can be prepared by conventional methods. For example the synthesis of p-phenylcalix[4]arene is described in Juneja et al (*J.Am. Chem. Soc.* 1993 115:3818–3819). The synthesis of p[4-(2-hydroxyethyl)piperazinomethyl]calix[4]arene is described by Atwood et al (*Angew. Chem. Int. Ed. Engl.* 1993 32:1093–94).

Other suitable complexing agents are a cyclotriveratrylene complexing agent of formula II

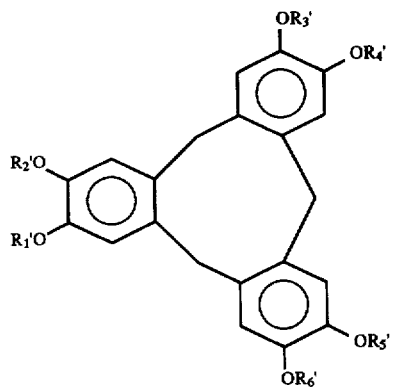

where $R_1'$–$R_6'$ are each independently H, $C_{1-20}$ alkyl, benzyl, $C_{1-20}$ alkyl substituted benzyl or $C_{6-20}$ aryl; or a cyclotetraveratrylene complexing agent of formula III

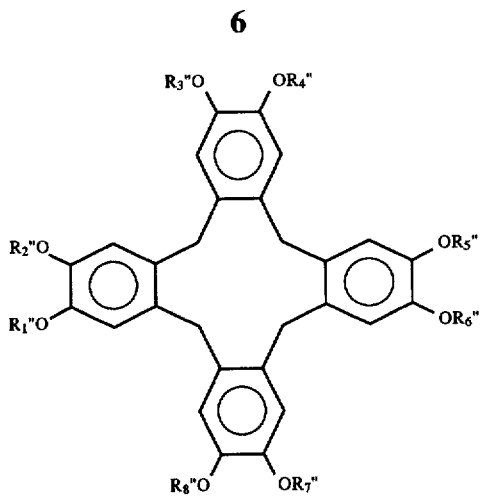

where $R_1''$–$R_8''$ are each independently H, $C_{1-20}$ alkyl, benzyl, $C_{1-20}$ alkyl substituted benzyl or $C_{6-20}$ aryl.

Suitable cyclotriveratrylene complexing agents of formula II are the compunds where $R_1'$–$R_6'$ are each H, $C_{1-6}$ alkyl and benzyl, preferably H, $CH_3$ and benzyl.

Suitable cyclotetraveratrylene complexing agents of formula II are the compunds where $R_1'$–$R_6'$ are each H, $C_{1-6}$ alkyl and benzyl, preferably H, $CH_3$ and benzyl.

Suitable cyclotriveratrylenes and cyclotetraveratrylenes can be synthesized by conventional methods known to those of ordinary skill in the art.

Suitable complexing agents are also resorcinol derived calixarenes of the formula IV

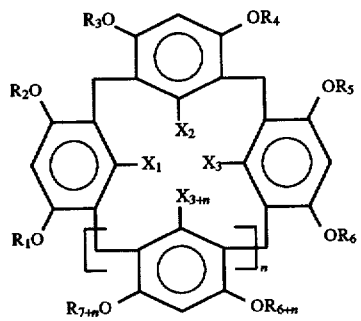

wherein
$R_1$-$R_{3+n}$ are each independently H, primary $C_{1-20}$ alkyl, secondary $C_{3-20}$ alkyl, tertiary $C_{4-20}$ alkyl, $C_{1-20}$ alkoxy, $C_{1-20}$ thioalkyl, $C_{6-20}$ aryl, $C_{6-20}$ aryloxy, $C_{6-20}$ aryl, nitro, halogen and $CH_2NR^1{}_2$ where $R^1$ is a $C_{1-20}$ alkyl;

$X_1$-$X_{3+n}$ are each independently H, OH, SH, $C_{1-20}$ alkoxy, $C_{1-20}$ thioalkyl, $C_{6-20}$ aryloxy, $OC(O)C_{1-20}$ alkyl and $C_{2-20}$ alkenyloxy; and n is an integer of 1 to 11, preferably 1–7, more preferably 1–5.

Preferably $R_1$-$R_{3+n}$ may be hydrogen, methyl, ethyl, propyl, isopropyl, butyl, iso-butyl, sec-butyl, tert-butyl, phenyl, xylyl, phenyoxy, naphthyl, benzyl, fluorine, chlorine, bromine, iodine, methoxy, ethoxy, propoxy butoxy, N,N-dimethyl methyleneamine, N,N-diethyl methyleneamine, N,N-dipropyl methyleneamine, N,N-diphenyl methyleneamine, $C_{6-20}$ aryl, $NO_2$ and $CH_2NR^1{}_2$ where $R^1$ is a $C_{1-20}$ alkyl.

Preferably $X_1$-$X_{3+n}$ may be H, OH, methoxy, ethoxy and propoxy.

The resorcinol derived calixarenes can be prepared by conventional methods known to those of ordinary skill in the art.

Suitable complexing agents are also oxacalixarenes, in which the two or more of the individual arene groups of formula I, are separated by an oxygen atom. Accordingly a suitable oxacalixarene is analogous to the compound of formula I, in which one or more of the methylene groups, which bridge the individual arene groups, is replaced by an oxygen atom.

The oxacalixarenes can be prepared by conventional methods known to those of ordinary skill in the art, for examples as described in Gutsthe (*Calixarenes, Royal Soc. Chem.* 1989 p. 61).

Suitable complexing agents are also homooxacalixarenes, in which the individual arene groups are separated by one or more 2-propyleneoxy groups, such as p-Bu$^t$dihomooxacalix[4]arene of the formula V

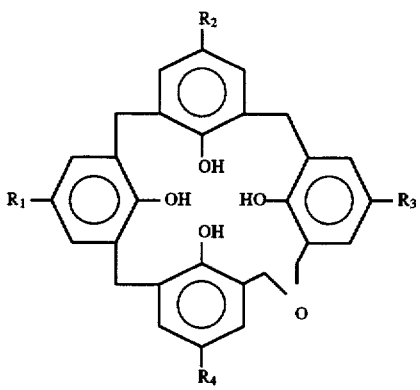

tetrahomodioxacalix[4]arene (*Gutsche J.Org. Chem.* (1983), 48:1536) and the cyclic trimer formed from 2,6-hydroxymethylphenol (*Gutsche J.Org. Chem.* (1983), 48:1536).

The homooxacalixarenes can be prepared by conventional methods known to those of ordinary skill in the art. The synthesis of p-Bu$^t$dihomooxacalix[4]arene and tetrahomodioxacalix[4]arene are reported in Gutsche (*Calixarenes, Royal Soc. Chem.* 1989 pp.61–62).

The complexing agent used to practice the claimed invention has a low degree of water solubility and is soluble in organic solvents. The complexing agent of the present invention preferably has a water solubility at 23° C. of ≦0.01 mol/L, more preferably ≦0.001 mol/L, even more preferably ≦0.0001 mol/L, most preferably ≦0.00001 mol/L.

The complex of the fullerene and the complexing agent is preferably formed in an aromatic solvent such as toluene, xylenes, benzene or a mixture thereof. Toluene is most preferred.

Of the aromatic solvents, the choice of toluene for complex formation is preferred. Complex of $C_{60}$ and p-Bu$^t$-calix[8]arene 3 is slightly soluble in toluene at ambient temperature, affording yellow solutions whereas above ca 80° C. it decomposes, as judged by the formation of magenta solutions characteristic of free fullerene-60 in toluene, and UV-visible spectroscopy. Dilute solutions of 3 in toluene at ambient temperature also contain free fullerene-60 (see FIG. 2). Xylenes and mesitylene rapidly decompose the complex 3 at 20° C. yielding free fullerene and calixarene on evaporation. Greater solvation of the fullerene-60 by the more electron rich arenes may be at the expense of complex formation. The fullerene-complexing agent complex is preferably formed at a temperature of anywhere from the melting temperature of the solvent to the reflux temperature of the solvent. Typically the fullerene-complexing agent complex is formed in refluxing toluene.

Recrystallization of the fullerene-complexing agent complex is achieved by filtering the hot fullerene-complexing agent complex, followed by cooling. A seed crystal of the fullerene-complexing agent complex can be added, if necessary.

After the fullerene-complexing agent has crystallized, the complex is isolated by filtration.

The fullerene-complexing agent complex can be decomposed, by introduction of a chlorinated hydrocarbon solvent, a fluoro hydrocarbon solvent or a chlorofluoro hydrocarbon solvent. Preferably solvents such as chloroform, dichloromethane and 1,2-dichloroethane are used.

In addition, the fullerene-complexing agent complex can be decomposed by the addition of a base to a solution of the fullerene-complexing agent complex in an aromatic solvent. Suitable bases include inorganic bases such as NaOH, KOH, $Ca(OH)_2$, $CaCO_3$, $K_2CO_3$ and organic bases such a amines. It is not necessary that the inorganic base be soluble in the aromatic solvent. Pellets of NaOH are preferred.

Complex 3 rapidly decomposes in chloroform which allows for an easy removal of fullerene-60 as a black precipitate (>95% recovery) from the calixarene which crystallizes as a suspended solid (relative densities: fullerene-60>chloroform>p-Bu$^t$-calix[8]arene. Fullerene-60 has only sparing solubility in chloroform (0.16 mg/mL), and the procedure allows for recovery of the calixarene, either as a solid directly, or as a mixture of fullerene and calixarene on removal of the solvent in vacuo. Dichloromethane and 1,2-dichloroethane also result in decomposition of the complex, whereas the complex is stable in carbon tetrachloride and t-butyl chloride. The absence of hydrogen atoms attached to the carbon bearing a chloro group in these solvents, unlike that for the foregoing chlorinated solvents, relates to the ability of such hydrogen atoms to form significant interactions with aromatic π-rings.

Removal of the calixarene from the fullerene can also be achieved by refluxing a toluene solution over sodium hydroxide pellets for ca 10 minutes (see FIG. 1), the calixarene separating as a sodium salt which fails to form a complex on cooling presumably because of disruption of the cavity.

In another embodiment of the present invention, a process of purifying and separation of fullerenes is provided by forming a complex of a fullerene and a complexing agent, wherein the complexing agent is immobilized.

Immobilization of the complexing agent may be by any means, wherein immobilization does not prevent formation of a complex with a fullerene. For example, in the case of the calixarenes and derivatives thereof, immobilization may be by coupling through the R group, to the immobilized support. The R group may be bonded directly to the immobilized support, or may be bonded through a linking group capable of binding to both the complexing agent and the immobilized support. Alternatively, binding of the calixarene to the immobilized support may be through one of the -OH groups at the para position to the R group.

In the case of the cycloveratrylenes, immobilization may be by coupling thorough the R' or R" group, to the immobilized support. The R' or R" group may be bonded directly to the immobilized support, or may be bonded through a linking group capable of binding to both the complexing agent and the immobilized support.

Suitable immobilized supports include for example polystyrene, polyester, polyamide, poly(meth) acrylate, polyurethane and polyvinyl chloride. The immobilized support must be such that when the complexing agent is bound to the immobilized support, the material is insoluble in organic solvents, particularly aromatic solvents.

Purification using the immobilized complexing agent may be performed using the immobilized complexing agent as a chromatographic support. The column of the immobilized complexing agent is treated with crude fullerene to be purified, under conditions sufficient to form a complex of the fullerene with the immobilized complexing agent. Once the complex is formed with the fullerene, and the impurities are washed away, the fullerene can be retrieved, by decomplexing with either a decomplexing solvent or a base as similarly describe above, for decomplexation of the fullerene-complexing agent complex.

Purification, using the immobilized complexing agent may also be performed by preparing a slurry of the immobilized complexing agent and the fullerene in an organic solvent, under conditions sufficient to form a complex of the fullerene with the immobilized complexing agent. After the complex of the fullerene and the immobilized complexing agent is formed, the slurry can be filtered to obtain the purified fullerene-immobilized complexing agent complex. The fullerene can be retrieved, by decomplexing with either a decomplexing solvent or a base as similarly describe above, for decomplexation of the fullerene-complexing agent complex.

Crude fullerene mixtures may be prepared by conventional mean, known to those of ordinary skill in the art. For example, according the the method described by *Kratschmer et al* (*Chem. Phys. Lett.* (1990), 170:167), a carbon rod is evaporated by resistive heating under a partial helium atmosphere (0.3 bar). A plasma discharge reactor for the synthesis of crude fullerenes is described by *Scrivens et al* (*J. Org. Chem* (1992), 57:6932–6936).

Overall the ability to selectively recover high purity fullerene-60 from carbon arc soot via simple complex/ recrystallization procedures, and also the enrichment of the fullerene-70 content of the residues is noteworthy. Moreover, formation of complex 3 as a sparingly soluble material is an attractive method of purifying fullerene-60 from crude fullerene mixtures and reaction mixtures.

Other features of the invention will become apparent in the course of the following descriptions of exemplary embodiments which are given for illustration of the invention and are not intended to be limiting thereof.

EXAMPLE 1

Synthesis of Complex p-Bu$^t$-calix[8]arene with $C_{60}$ and>99.5% Purity Fullerene-60.

In a typical experiment ca 7.5 g of fresh carbon arc soot was stirred with 250 mL of toluene for one hour then, the mixture was filtered, and 1.0 g of the p-Bu$^t$calix[8]arene added. After refluxing for 10 minutes the mixture was filtered, seeded with crystals of 3 then allowed to stand at ca 20° C. over night. The yellow/brown plates of the complex were then collected and recrystallized twice: from toluene (1.0 g from 80 mLs of toluene), 90% yield, analysis: found C 88.20, H 5.25%; calc. C 88.07 H 5.59%. Addition of chloroform (5 mLs) to the complex (0.85 g) afforded a precipitate of fullerene-60 (0.28 g, 92% recovery from the recrystallized complex).

EXAMPLE 2

Synthesis of Calix[6]arene($C_{60}$)$_2$. 6.

To a refluxing solution of fullerene-60 (5 mg) in toluene (5 mL) was added calix[6]arene (4.4 mg). The hot solution was rapidly filtered and slowly cooled overnight yielding black prisms (5.5 mg, 77% yield, analysis: found C 94.18 H 1.87% calc.; H 1.75 C 93.63%).

EXAMPLE 3

Synthesis of p-Bu$^t$-calix[6]arene($C_{70}$)$_2$. 7.

To a refluxing solution of fullerene-70 (5 mg) in toluene (2 mL) was added p-Bu$^t$-calix[6]arene (5.8 mg). The hot solution was rapidly filtered and slowly cooled overnight yielding red/brown needles (2.5 mg, 31% yield, analysis: found C 92.48, H 3.19% calc. C 93.2, H 3.19%).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the purification of $C_{60}$ and high fullerenes comprising
   (a) contacting a crude fullerene mixture in a first solvent with a complexing agent selected from the group consisting of a calixarene, an oxacalixarene, a homooxacalixarene, a cyclotriveratrylene, and a cyclotetraveratrylene to form a fullerene-complexing agent guest-host complex.
   (b) recrystallizing said fullerene-complexing agent complex from an organic solvent,
   (c) separating said fullerene from said fullerene-complexing agent complex; and
   (d) isolating said fullerene.

2. The process of claim 1 wherein said solvent is toluene.

3. The process of claim 1 wherein said organic solvent is toluene.

4. The process of claim 1 wherein said separation is by contacting said fullerene-complexing agent complex with chloroform.

5. The precess of claim 1 wherein said separation is by Contacting said fullerene-complexing agent complex with dichloromethane or 2-dichlorethane.

6. The process of claim 1 wherein said separation is by contacting said fullerene-complexing agent complex with sodium hydroxide.

7. The process of claim 1 wherein said complexing agent is of the formula I

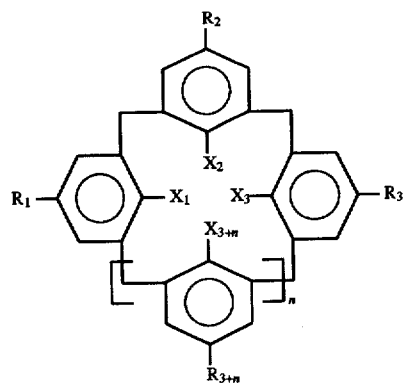

wherein $R_1$-$R_{3+n}$ are each independently H, primary $C_{1-20}$ alkyl, secondary $C_{3-20}$ alkyl, tertiary $C_{4-20}$ alkyl, $C_{1-20}$ alkoxy, $C_{1-20}$ thioalkyl, $C_{6-20}$ aryl, $C_{6-20}$ aryloxy, $C_{6-20}$ aryl, nitro, halogen and $CH_2NR^1_2$ where $R^1$ is a $C_{1-20}$ alkyl;

$X_1$-$X_{3+n}$ are each independently H, OH, SH, $C_{1-20}$ alkoxy, $C_{1-20}$ thioalkyl, $C_{6-20}$ aryloxy, $OC(O)C_{1-20}$ alkyl, $C_{2-20}$ alkenyloxy; and n is an integer of 1 to 11.

8. The process of claim 7, wherein n is an integer of 1 to 7.

9. The process of claim 7, wherein n is an integer of 1 to 5.

10. The process of claim 7, wherein $R_1$-$R_{3+n}$ is hydrogen, methyl, ethyl, propyl, isopropyl, butyl, iso-butyl, sec-butyl, tert-butyl, phenyl, xylyl, phenyoxy, naphthyl, benzyl, fluorine, chlorine, bromine and iodine, methoxy, ethoxy, propoxy butoxy, N,N-dimethyl methyleneamine, N,N-diethyl methyleneamine, N,N-dipropyl methyleneamine, N,N-diphenyl methyleneamine, $C_{6-20}$ aryl, $NO_2$ and $CH_2NR^1_2$ where $R^1$ is a $C_{1-20}$ alkyl.

11. The process of claim 1, wherein said complexing agent is of the formula II

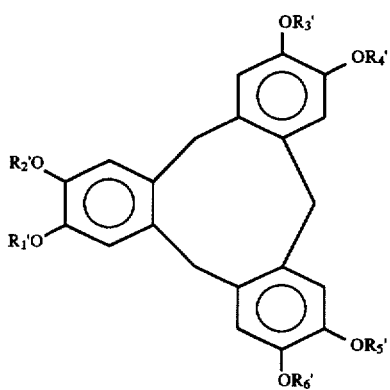

where R' is H, $C_{1-20}$ alkyl, benzyl, $C_{1-20}$ alkyl substituted benzyl or $C_{6-20}$ aryl; or a complexing agent of the formula III

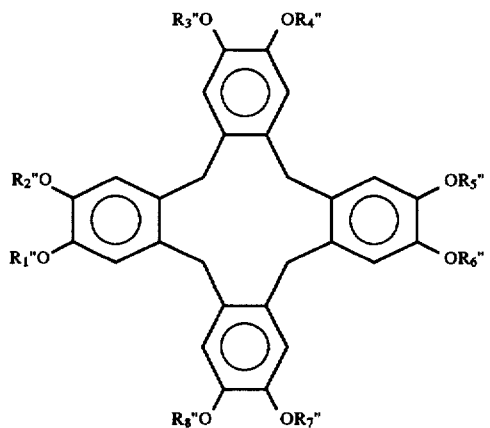

where R" is H, $C_{1-20}$ alkyl, benzyl, $C_{1-20}$ alkyl substituted benzyl or $C_{6-20}$ aryl.

12. A process for the separation and purification of a mixture of $C_{60}$ and $C_{70}$ in a solvent with a complexing agent to form a fullerene $C_{60}$ and $C_{70}$-complexing agent complex, (a) contacting a fullerene mixture of $C_{60}$ and $C_{70}$ in a first solvent with a complexing agent selected from the group consisting of a calixarene, an oxacalixarene, a homooxacalixarene, a cyclotriveratrylene, and a cyclotetraveratrylene to form a fullerene $C_{60}$ and $C_{70}$-complexing agent guest-host complex.

(b) recrystallizing said fullerene $C_{60}$ and $C_{70}$-complexing agent complex from an organic solvent, and (c) separating said fullerene $C_{60}$ and $C_{70}$ from said fullerene $C_{60}$ and $C_{70}$-complexing agent complex; and (d) isolating said fullerene $C_{60}$ and $C_{70}$.

13. The process of claim 12 wherein said complexing agent is a cyclotriveratrylene.

14. The process of claim 12 wherein said first solvent is toluene.

15. The process of claim 12 wherein said organic solvent is toluene.

16. The process of claim 15 wherein said separation is by contacting said fullerene $C_{60}$ and $C_{70}$-complexing agent complex with chloroform.

17. The process of claim 15 wherein said separation is by contacting said fullerene $C_{60}$ and $C_{70}$-complexing agent complex with dichloromethane or 1,2-dichloroethane.

18. The process of claim 15 wherein said separation is by contacting said fullerene $C_{60}$ and $C_{70}$-complexing agent complex with sodium hydroxide.

19. The process of claim 12 wherein said complexing agent is calix(6)arene.

20. A process for the separation and purification of $C_{60}$ and higher fullerenes comprising (a) contacting a crude fullerene mixture in a first solvent with an immobilized complexing agent to form an immobilized fullerene-complexing agent guest-host complex;

(b) separating said immobilized fullerene-complexing agent complex from said solvent; and (c) separating said fullerene from said immobilized fullerene-complexing agent complex;

wherein said complexing agent is selected from the group consisting of a calixarene, an oxacalixarene, a homooxacalixarene, a cyclotriveratrylene, and a cyclotetraveratrylene.

21. The process of claim 20, wherein said immobilized complexing agent is immobilized on a resin support.

22. The process of claim 20 wherein said separation is carried out above ambient temperature by contacting said immobilized fullerene-complexing agent complex with a decomplexing solvent.

23. The process of claim 20 wherein said separation is carried out above ambient temperature without a decomplexing solvent.

24. The process of claim 20, wherein said calixarene is a resorcinol derived calixarene characterized by the formula IV

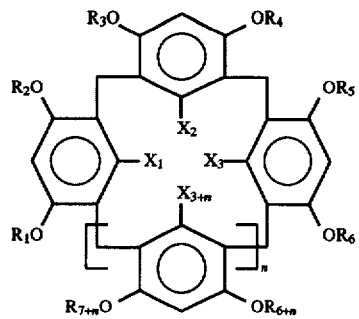

wherein $R_1$-$R_{3+n}$ are each independently H, primary $C_{1-20}$ alkyl, secondary $C_{3-20}$ alkyl, tertiary $C_{4-20}$ alkyl, $C_{1-20}$ alkoxy, $C_{1-20}$ thioalkyl, $C_{6-20}$ aryl, $C_{6-20}$ aryloxy, $C_{6-20}$ aryl, nitro, halogen or $CH_2NR^1_2$ where $R^1$ is a $C_{1-20}$ alkyl;

$X_1$-$X_{3+n}$ are each independently H, OH, SH, $C_{1-20}$ alkoxy, $C_{1-20}$ thioalkyl, $C_{6-20}$ aryloxy, $OC(O)C_{1-20}$ alkyl, or $C_{2-20}$ alkenyloxy; and n is an integer of 1 to 11.

25. In a process for the purification of a first fullerene from a crude fullerene mixture of said first fullerene and at least a second fullerene, the steps comprising:
   (a) providing a complexing agent selected from the group consisting of a calixarene, an oxacalixarene, a homooxacalixarene, a cyclotriveratrylene, and a cyclotetratriveratrylene, which agent is soluble in an organic aromatic solvent and has a water solubility at 23° C. of less than 0.01 mol/L, said complexing agent having a preferential selectivity for said first fullerene relative to said second fullerene in said crude fullerene mixture;
   (b) providing an organic solvent;
   (c) contacting said crude fullerene mixture and said completing agent in said organic solvent to form a fullerene-complexing agent guest-host complex in which said first fullerene is preferentially complexed relative to said second fullerene;
   (d) precipitating said guest-host complex in said organic solvent;
   (e) recovering said precipitated guest-host complex from said organic solvent;
   (f) recrystallizing said precipitated guest host complex;
   (g) recovering said recrystallized complex from step (f); and
   (h) decomposing said guest-host complex to recover the fullerene content of said guest-host complex.

26. The process of claim 25 wherein the organic solvent in step (b) and in step (f) is an aromatic solvent selected from the group consisting of toluene, xylene, benzene, and mixtures thereof.

27. The method of claim 26 wherein the decomposition of said guest-host complex in step (h) is effected by contacting said complex with a chlorinated hydrocarbon solvent, a fluorohydrocarbon solvent, or a chlorofluorohydrocarbon solvent.

28. The process of claim 27 wherein said solvent is chlorinated solvent selected from the group consisting of chloroform, dichloromethane, and 1,2-dichlorethane.

29. The process of claim 25 wherein said complexing agent is a calixarene characterized by the formula

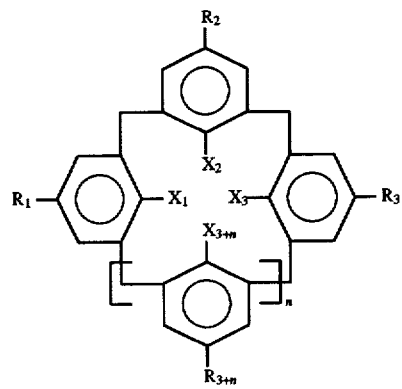

wherein $R_1$-$R_{3+n}$ are each independently H, primary $C_{1-20}$ alkyl, secondary $C_{3-20}$ alkyl, tertiary $C_{4-20}$ alkyl, $C_{1-20}$ alkoxy, $C_{1-20}$ thioalkyl, $C_{6-20}$ aryl, $C_{6-20}$ aryloxy, $C_{6-20}$ aryl, nitro, halogen or $CH_2NR^1_2$ where $R^1$ is a $C_{1-20}$ alkyl;

$X_1$-$X_{3+n}$ are independently H, OH, SH, $C_{1-20}$ alkoxy, $C_{1-20}$ thioalkyl, $C_{6-20}$ aryloxy, $OC(O)C_{1-20}$ alkyl, $C_{2-20}$ alkenyloxy; and n is an integer of 1 to 7.

30. The process of claim 29 wherein each X-$X_{3+n}$ is OH, and each $R_1$-$R_{3+n}$ is an alkyl group selected from the group consisting of methyl, ethyl, propyl, isopropyl, isobutyl, secondary butyl, and tertiary butyl.

31. The process of claim 29 wherein said crude fullerene mixture contains fullerene $C_{60}$ as the designated fullerene.

32. The process of claim 30 wherein said at least one other fullerene contains fullerene $C_{70}$ and said calixarene is tertiary butyl calix(8)arene which preferentially complexes fullerene $C_{60}$ relative to fullerene $C_{70}$.

33. The process of claim 25 wherein said complexing agent is a calix(8)arene and said crude fullerene mixture comprises a mixture of fullerene $C_{60}$ and fullerene $C_{70}$.

* * * * *